(12) United States Patent
Loo

(10) Patent No.: US 11,806,086 B2
(45) Date of Patent: Nov. 7, 2023

(54) ENDOSCOPY SYSTEM

(71) Applicant: ALTEK BIOTECHNOLOGY CORPORATION, Hsinchu (TW)

(72) Inventor: Hsi-Hsin Loo, Taipei (TW)

(73) Assignee: ALTEK BIOTECHNOLOGY CORPORATION, Hsinchu (TW)

( * ) Notice: Subject to any disclaimer, the term of this patent is extended or adjusted under 35 U.S.C. 154(b) by 272 days.

(21) Appl. No.: 17/023,393

(22) Filed: Sep. 17, 2020

(65) Prior Publication Data

US 2021/0251695 A1 Aug. 19, 2021

(30) Foreign Application Priority Data

Feb. 13, 2020 (TW) .................................. 109201563

(51) Int. Cl.
*A61B 34/20* (2016.01)
*A61B 5/06* (2006.01)
(Continued)

(52) U.S. Cl.
CPC .......... *A61B 34/20* (2016.02); *A61B 1/00004* (2013.01); *A61B 1/01* (2013.01);
(Continued)

(58) Field of Classification Search
None
See application file for complete search history.

(56) References Cited

U.S. PATENT DOCUMENTS

| 6,517,484 B1 | 2/2003 | Wilk et al. |
| 2002/0183592 A1 | 12/2002 | Suzuki et al. |

(Continued)

FOREIGN PATENT DOCUMENTS

| CN | 108697457 | 10/2018 | |
| DE | 102015104821 A1 * | 9/2016 | ......... A61B 17/3421 |

(Continued)

OTHER PUBLICATIONS

DE-102015104821-A1 translation (Year: 2016).*
(Continued)

*Primary Examiner* — Jason M Ip
*Assistant Examiner* — Renee C Langhals
(74) *Attorney, Agent, or Firm* — JCIPRNET

(57) ABSTRACT

An endoscopy system including a flexible insertion tube, a motion sensing module and a processor is provided. The flexible insertion tube has a central axis. The motion sensing module includes a housing, patterns and sensors. The patterns are disposed at a surface of the flexible insertion tube according to an axial orientation distribution and an angle distribution based on the central axis. The sensors are disposed in the housing and located beside a guiding hole of the housing. The processor is disposed in the housing. During relative motion of the flexible insertion tube with respect to the motion sensing module via the guiding hole, the sensors are configured to sense a motion state of the patterns so as to obtain a motion-state sensing result. The processor determines insertion depth information and insertion tube rotating angle information according to the motion-state sensing result, the axial orientation distribution and the angle distribution.

17 Claims, 12 Drawing Sheets

(51) Int. Cl.
  *A61B 90/00* (2016.01)
  *A61B 1/05* (2006.01)
  *A61B 1/01* (2006.01)
  *A61B 1/00* (2006.01)

(52) U.S. Cl.
  CPC ............... *A61B 1/05* (2013.01); *A61B 5/062* (2013.01); *A61B 90/06* (2016.02); *A61B 2034/2055* (2016.02); *A61B 2034/2065* (2016.02); *A61B 2090/062* (2016.02)

(56) References Cited

U.S. PATENT DOCUMENTS

| | | | |
|---|---|---|---|
| 2003/0052169 | A1 | 3/2003 | Tsikos et al. |
| 2003/0176770 | A1 | 9/2003 | Merril et al. |
| 2003/0208103 | A1* | 11/2003 | Sonnenschein ........ A61B 90/06 600/117 |
| 2004/0111081 | A1 | 6/2004 | Whitman et al. |
| 2009/0090763 | A1* | 4/2009 | Zemlok ............ A61B 17/07207 227/175.2 |
| 2015/0265367 | A1* | 9/2015 | Gruhler ............ A61B 17/00234 600/424 |
| 2016/0287241 | A1* | 10/2016 | Azevedo ............ A61B 5/1076 |
| 2017/0157361 | A1 | 6/2017 | Barrish et al. |
| 2018/0240237 | A1* | 8/2018 | Donhowe ............. G06T 7/0014 |
| 2019/0343371 | A1* | 11/2019 | Brooks ................ A61B 1/0684 |
| 2020/0004008 | A1 | 1/2020 | Chen |

FOREIGN PATENT DOCUMENTS

| | | |
|---|---|---|
| EP | 3061408 | 8/2016 |
| EP | 3381348 | 10/2018 |
| JP | 2002153472 | 5/2002 |
| JP | 2013061558 | 4/2013 |
| TW | 201106089 | 2/2011 |
| TW | 201121488 | 7/2011 |
| TW | 201922179 | 6/2019 |
| WO | 2017030913 | 2/2017 |
| WO | 2018144726 | 8/2018 |
| WO | 2019139841 | 7/2019 |

OTHER PUBLICATIONS

Office Action of Taiwan Counterpart Application, dated Oct. 6, 2021, pp. 1-3.
"Office Action of China Counterpart Application", dated May 5, 2022, p. 1-p. 7.
"Notice of allowance of China Related Application, Application No. 202110176652.0", dated Jul. 14, 2022, p. 1-p. 4.

* cited by examiner

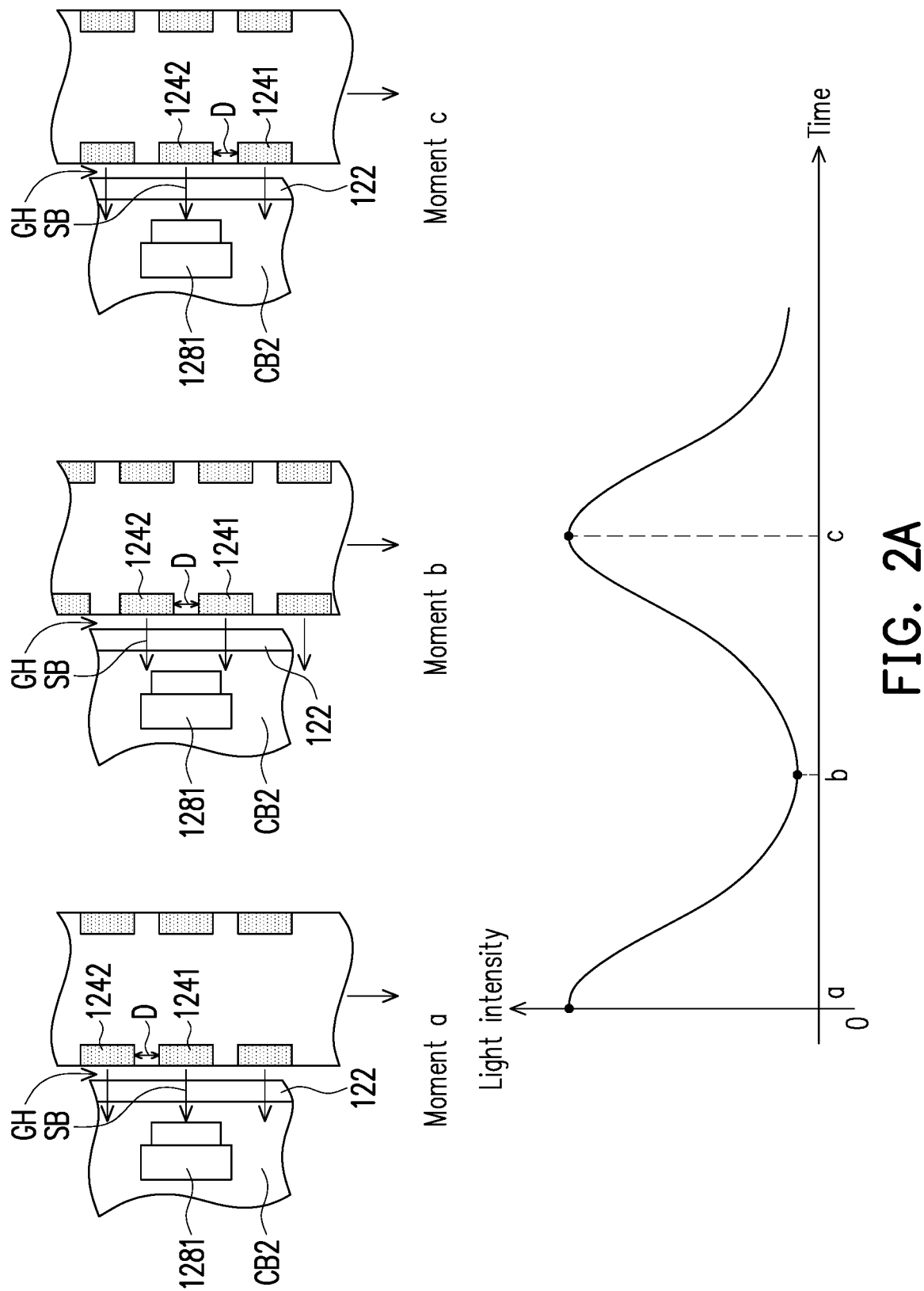

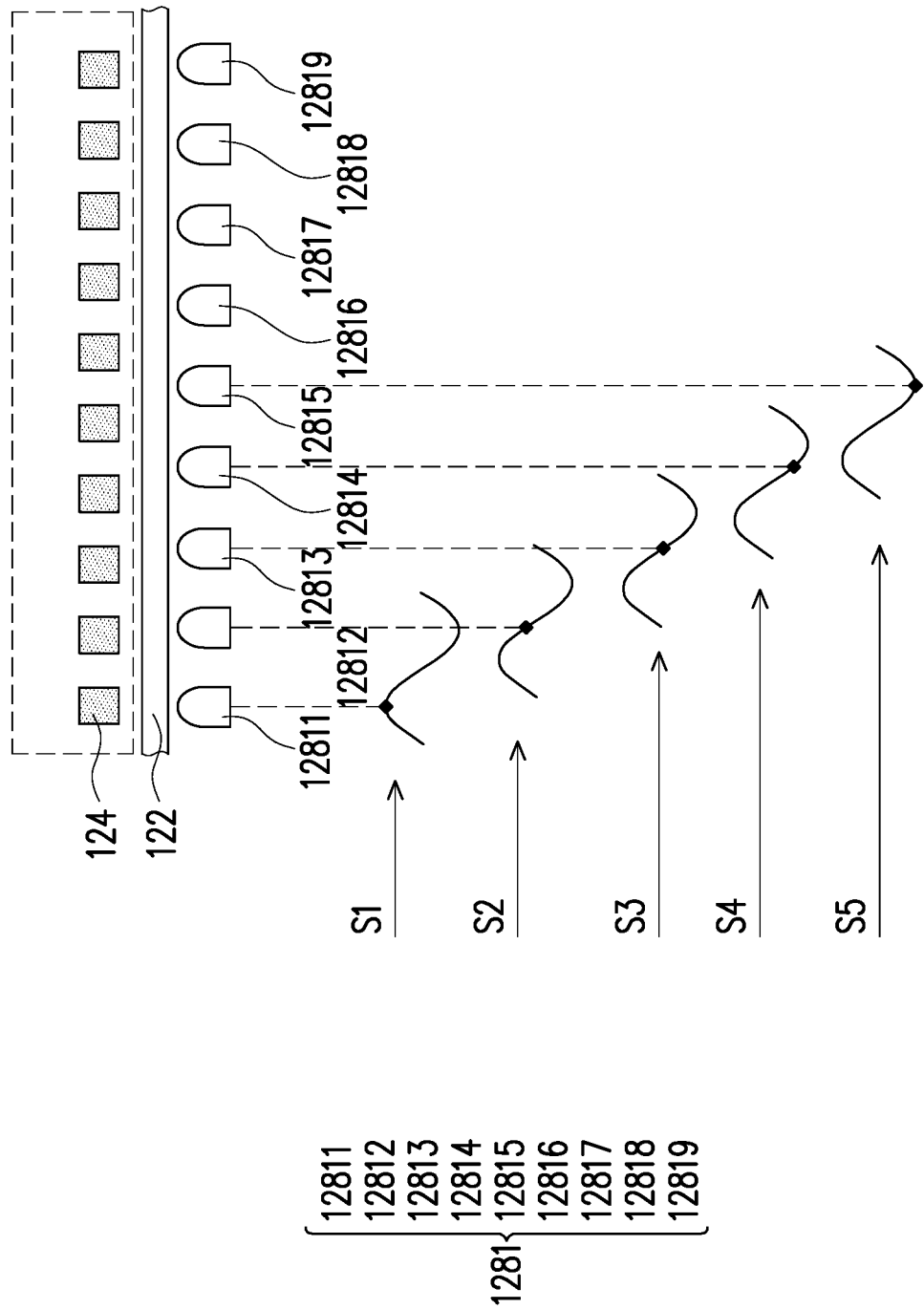

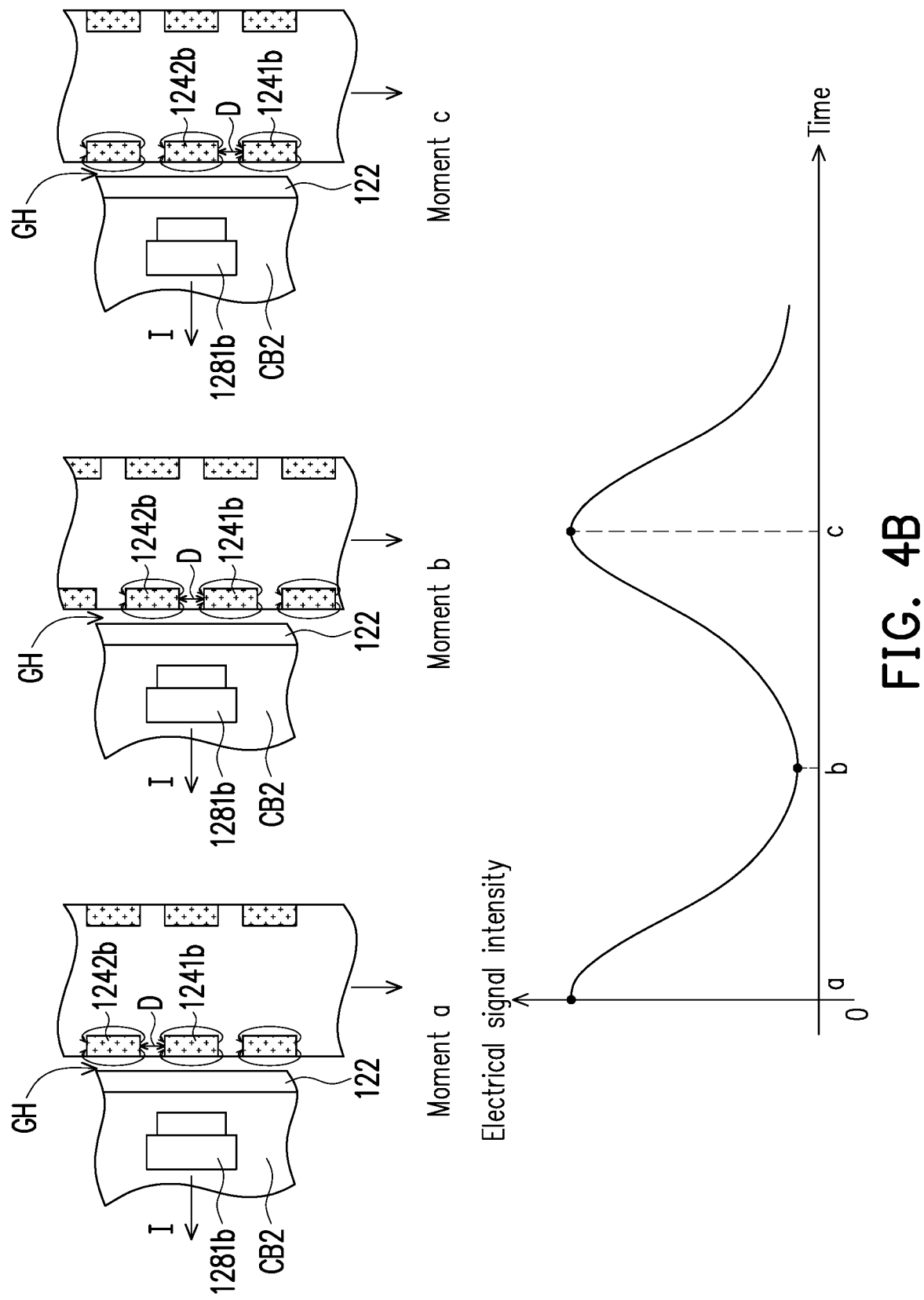

ENDOSCOPY SYSTEM

CROSS-REFERENCE TO RELATED APPLICATION

This application claims the priority benefit of Taiwan application serial no. 109201563, filed on Feb. 13, 2020. The entirety of the above-mentioned patent application is hereby incorporated by reference herein and made a part of this specification.

BACKGROUND

Technical Field

The disclosure relates to an endoscopy system, and more particularly, to an endoscopy system capable of obtaining insertion depth information and insertion tube rotating angle information.

Description of Related Art

An endoscope is an instrument that can be inserted into a human body to diagnose the inside of an organ. Generally, an endoscope is provided with a lens at one end of an insertion tube, and the medical personnel introduce the lens into the human body through the insertion tube to capture an image of the inside of the human body. However, the existing endoscope cannot detect an insertion depth and a rotating angle of the insertion tube. It is difficult for the medical personnel to know an exact location of a lesion. The above information must be obtained with the assistance of other systems. Therefore, when a patient is diagnosed or treated next time, the medical personnel need to spend more time to find lesions found in the previous diagnosis or treatment. It is difficult to achieve accurate medical treatment with the existing endoscope alone, and the diagnostic timeliness is not ideal.

SUMMARY

The disclosure provides an endoscopy system, which may obtain related information such as an insertion depth and a rotating angle of a flexible insertion tube, may achieve accurate medical treatment and has good diagnostic timeliness.

The disclosure provides an endoscopy system, including a flexible insertion tube, a motion sensing module and an imaging device. The flexible insertion tube has a central axis. The motion sensing module includes a housing, a plurality of patterns, a plurality of signal sensors, and a processor. The housing has a guiding hole. The patterns are disposed at a surface of the flexible insertion tube according to an axial orientation distribution and an angle distribution based on the central axis. The sensors are disposed in the housing and located beside the guiding hole. The processor is disposed in the housing and electrically connected to the sensors. During the relative motion of the flexible insertion tube with respect to the motion sensing module via the guiding hole, the sensors are configured to sense a motion state of the patterns so as to obtain a motion-state sensing result. The processor determines insertion depth information and insertion tube rotating angle information according to the motion-state sensing result, the axial orientation distribution and the angle distribution. The imaging device is disposed at one end of the flexible insertion tube.

In one embodiment of the disclosure, the sensors further include a plurality of depth sensors and a plurality of rotating angle sensors. The depth sensors are disposed in an extension direction of the guiding hole, and the rotating angle sensors are disposed around the guiding hole. The depth sensors are configured to sense an axial motion state of the patterns along an axial orientation of the central axis so as to obtain an axial motion sensing result of the patterns. The processor determines the insertion depth information according to the axial motion sensing result and the axial orientation distribution. The rotating angle sensors are configured to sense a rotating motion state of the patterns rotating with respect to the motion sensing module so as to obtain a rotating motion sensing result of the patterns. The processor determines the insertion tube rotating angle information according to the rotating motion sensing result and the angle distribution.

In one embodiment of the disclosure, the motion sensing module further includes a plurality of first light emitting members. The sensors are a plurality of light sensors. Each of the first light emitting members is configured to emit a sensing beam.

In one embodiment of the disclosure, the first light emitting members are integrated into the patterns respectively so that the patterns are a plurality of light emitting patterns. During the relative motion of the flexible insertion tube with respect to the motion sensing module via the guiding hole, the light emitting patterns emit the sensing beams from the flexible insertion tube to be transmitted to the depth sensors and the rotating angle sensors to obtain the axial motion sensing result and the rotating motion sensing result.

In one embodiment of the disclosure, the first light emitting members are integrated into the light sensors respectively. The patterns are a plurality of reflection patterns. During the relative motion of the flexible insertion tube with respect to the motion sensing module via the guiding hole, the first light emitting members emit the sensing beams to the reflection patterns from where the light sensors are located. The reflection patterns reflect the sensing beams, and the reflected sensing beams are transmitted to the depth sensors and the rotating angle sensors to obtain the axial motion sensing result and the rotating motion sensing result.

In one embodiment of the disclosure, the patterns are a plurality of magnetic patterns, the sensors are a plurality of induction coils, the depth sensors are a plurality of depth induction coils, and the rotating angle sensors are a plurality of rotating angle induction coils. During the relative motion of the flexible insertion tube with respect to the motion sensing module via the guiding hole, the depth induction coils and the rotating angle induction coils sense a magnetic field change of the magnetic patterns to induce at least one induced current, and the depth induction coils and the rotating angle induction coils obtain the axial motion sensing result and the rotating motion sensing result according to the at least one induced current.

In one embodiment of the disclosure, the patterns are a plurality of magnetic patterns. The sensors are a plurality of Hall sensors, the depth sensors are a plurality of depth Hall sensors, and the rotating angle sensors are a plurality of rotating angle Hall sensors. During the relative motion of the flexible insertion tube with respect to the motion sensing module via the guiding hole, the depth Hall sensors and the rotating angle Hall sensors sense a magnetic field change of the magnetic patterns to induce at least one induced voltage, and the depth Hall sensors and the rotating angle Hall sensors obtain the axial motion sensing result and the rotating motion sensing result according to the at least one induced voltage.

In one embodiment of the disclosure, the motion sensing module further includes a first angle sensor, disposed in the housing. The first angle sensor is electrically connected to the processor. The first angle sensor is configured to sense first angle information of the motion sensing module and transmit the first angle information to the processor.

In one embodiment of the disclosure, the motion sensing module further includes a first circuit board and a second circuit board disposed in the housing. The first circuit board is electrically connected to the depth sensors, and the second circuit board is electrically connected to the rotating angle sensors.

In one embodiment of the disclosure, the motion sensing module further includes a timer. The timer is electrically connected to the processor and configured to transmit time information to the processor. The processor determines speed information of the flexible insertion tube according to the time information and the insertion depth information. The processor determines angular speed information of the flexible insertion tube according to the time information and the insertion tube rotating angle information.

In one embodiment of the disclosure, a spatial frequency of the sensors is different from a spatial frequency of the patterns.

In one embodiment of the disclosure, the axial orientation distribution is an equal pitch distribution.

In one embodiment of the disclosure, the angle distribution is an equal angle distribution.

In one embodiment of the disclosure, the endoscopy system further includes a second angle sensor. The second angle sensor is disposed at the end of the flexible insertion tube and located beside the imaging device. The second angle sensor is electrically connected to the processor and configured to sense second angle information of the end of the flexible insertion tube.

In one embodiment of the disclosure, the endoscopy system further includes a steering lever. The steering lever is disposed at another end of the flexible insertion tube and coupled to the flexible insertion tube. The steering lever is configured to control an angle of a distal segment in the flexible insertion tube.

In one embodiment of the disclosure, the endoscopy system further includes a third angle sensor. The third angle sensor is disposed on the steering lever. The third angle sensor is electrically connected to the processor and configured to sense third angle information of the steering lever.

In one embodiment of the disclosure, the imaging device further includes an imaging lens, a second light emitting member and an image sensor. The imaging lens is optically coupled to the image sensor, and the second light emitting member is configured to emit an illumination beam to illuminate an object to be detected. The object to be detected reflects at least a part of the illumination beam to the imaging lens, and the image sensor senses an image of the object to be detected.

Based on the above, in the endoscopy system according to the embodiments of the disclosure, a plurality of patterns of a motion sensing module is disposed at a surface of a flexible insertion tube according to an axial orientation distribution and an angle distribution, and a plurality of sensors is disposed in a housing and located beside a guiding hole. Therefore, a distance or angle relationship specified by the patterns is used as a quantitative basis for the description of a location or a motion state. During the relative motion of the flexible insertion tube with respect to the motion sensing module via the guiding hole, the sensors may sense a motion state of the patterns so as to obtain a motion-state sensing result. The processor then determines insertion depth information and insertion tube rotating angle information according to the motion-state sensing result, the axial orientation distribution and the angle distribution. Medical personnel may know the location of a lesion from the insertion depth information and the insertion tube rotating angle information. Therefore, the endoscopy system may achieve accurate medical treatment and has good diagnostic timeliness.

In order to make the foregoing features and advantages of the disclosure more comprehensible, embodiments are described below in detail with the accompanying drawings as follows.

BRIEF DESCRIPTION OF THE DRAWINGS

FIG. 2A is a schematic enlarged diagram of the flexible insertion tube of FIG. 1A to FIG. 1C during an axial motion and a time-varying diagram of a light intensity electrical signal measured by a corresponding depth sensor.

FIG. 2C is a schematic diagram of a configuration relationship between a plurality of depth sensors and a plurality of patterns and a light intensity electrical signal sensed by a depth sensor.

FIG. 4B is a schematic enlarged diagram of the flexible insertion tube of FIG. 4A during an axial motion and a time-varying diagram of an electrical signal measured by a corresponding depth sensor.

DESCRIPTION OF THE EMBODIMENTS

Figure 1A:
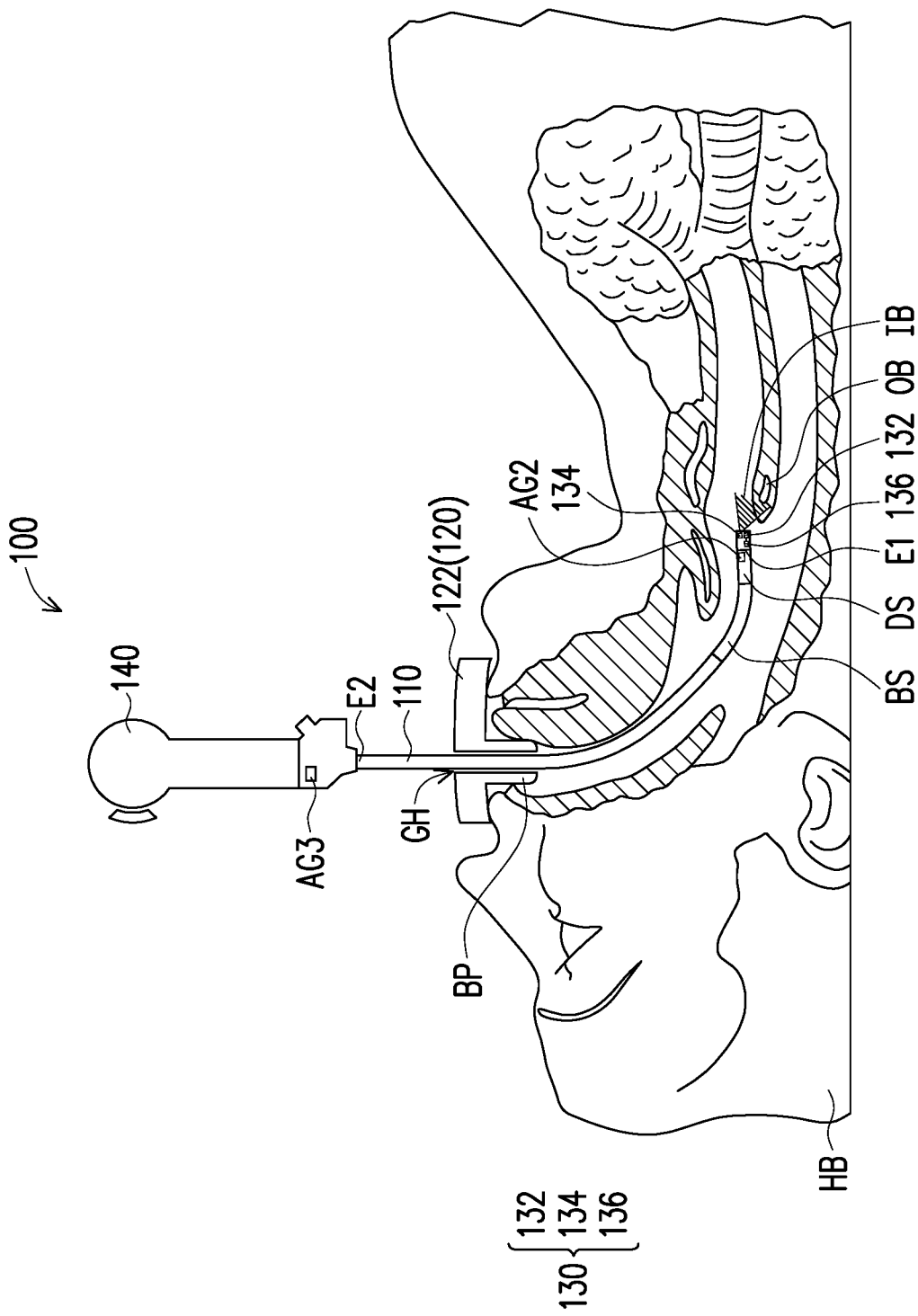
FIG. 1A is a schematic application diagram of an endoscopy system applied to a human body according to an embodiment of the disclosure.
Figure 1B:
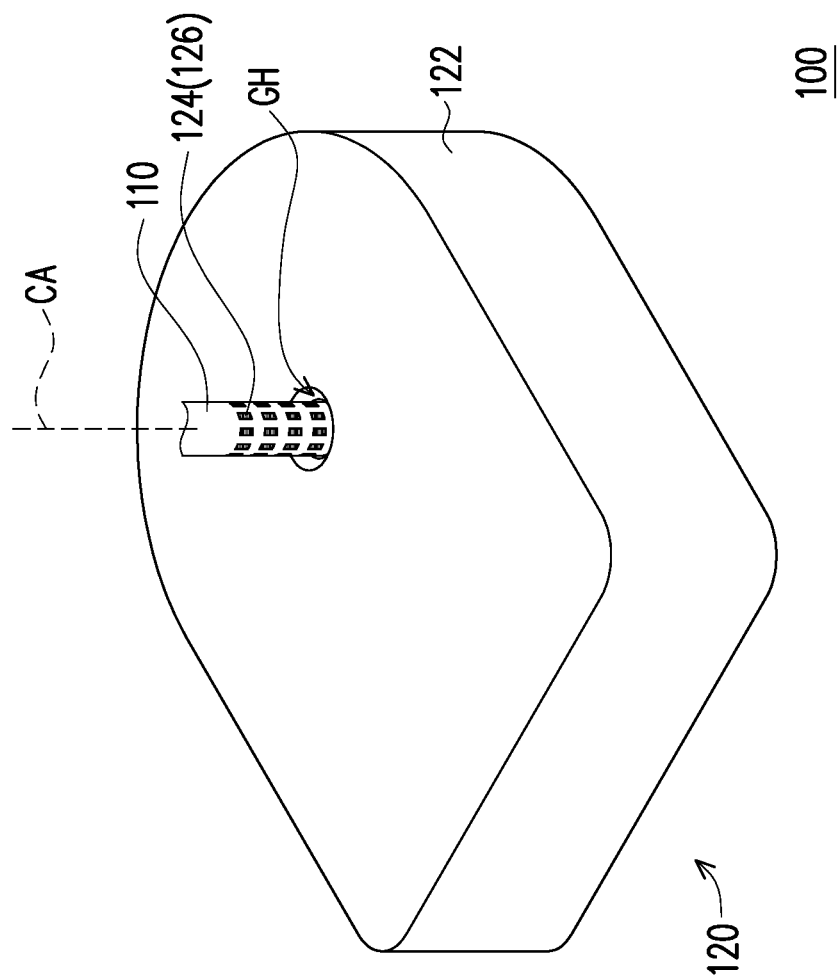
FIG. 1B is a schematic appearance diagram of a flexible insertion tube and a motion sensing module of FIG. 1A.
Figure 1C:
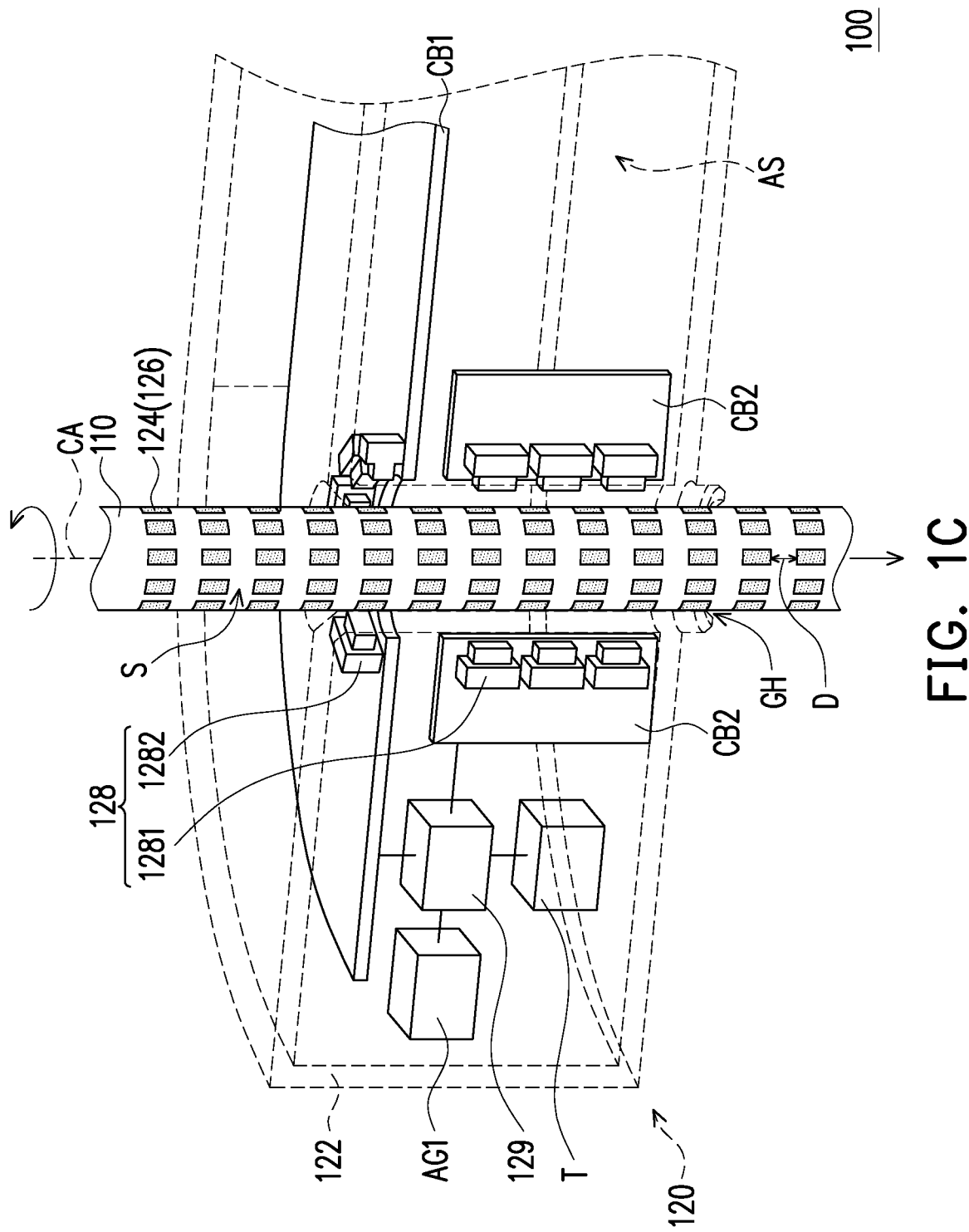
FIG. 1C is a schematic partial cross-sectional diagram of the endoscopy system in FIG. 1A.

FIG. 1A is a schematic application diagram of an endoscopy system applied to a human body according to an embodiment of the disclosure. FIG. 1B is a schematic appearance diagram of a flexible insertion tube and a motion sensing module of FIG. 1A. FIG. 1C is a schematic partial cross-sectional diagram of the endoscopy system in FIG. 1A.

Referring to FIG. 1A to FIG. 1C, in the present embodiment, the endoscopy system 100 is a medical instrument that enters a human body HB through an insertion tube to observe an internal condition of the human body HB. In detail, the endoscopy system 100 mainly includes a flexible insertion tube 110, a motion sensing module 120, an imaging device 130, and a steering lever 140. In the following paragraphs, a configuration manner among components will be described in detail.

The flexible insertion tube 110 is formed of a flexible material and has flexibility. As shown in FIG. 1B and FIG. 1C, the flexible insertion tube 110 has a central axis CA. An axial orientation referred to in the embodiments of the disclosure refers to an extension direction of the flexible insertion tube 110 along the central axis CA.

The motion sensing module 120 is a module capable of sensing a motion state of the flexible insertion tube 110 by a change in light intensity or a magnetic field. For the convenience of description, the following paragraphs will first take an optical motion sensing module as an example. In the present embodiment, the motion sensing module 120 is, for example, an optical motion sensing module, including a housing 122, a plurality of patterns 124, a plurality of first light emitting members 126, a plurality of sensors 128, a processor 129, a first circuit board CB1, a second circuit board CB2, and a timer T. In the following paragraphs, configurations among internal components of the motion sensing module 120 will be described in detail.

The housing 122 has an accommodating space AS therein for accommodating various components in the motion sensing module 120 and providing a protection function. The housing 122 has a guiding hole GH that communicates with the outside. The flexible insertion tube 110 may enter the human body HB through the guiding hole GH to capture an internal image of the human body HB.

The patterns 124 are disposed at a surface of the flexible insertion tube 110 according to an axial orientation distribution and an angle distribution based on the central axis CA. Specifically, the so-called "disposed at a surface S of the flexible insertion tube 110 according to an axial orientation distribution" means that the patterns 124 are disposed at the surface S of the flexible insertion tube 110 along an axial orientation of the central axis CA according to a specific pitch distribution. The specific pitch distribution is, for example, an equal pitch distribution, that is, in a direction parallel to the axial orientation of the central axis CA, distances D between any two of the patterns 124 are equal to each other, but the disclosure is not limited thereto. In addition, the so-called "disposed at a surface S of the flexible insertion tube 110 according to an angle distribution" means that the patterns 124 are disposed at the surface of the flexible insertion tube 110 by centering on the central axis CA according to a specific angle distribution. The specific angle distribution is, for example, an equal angle distribution, that is, included angles between any two of the patterns 124 relative to the central axis CA are equal to each other, but the disclosure is not limited thereto. The patterns 124 may be optionally disposed on an outer surface or an inner surface of the flexible insertion tube 110, but the disclosure is not limited thereto. Therefore, the patterns 124 have a specified distance or angle relationship as a quantitative basis for the description of a location or a motion state.

The first light emitting members 126 are optical members capable of emitting light functionally, which may be, for example, light emitting components that are electrically controlled to emit light or fluorescent members that are self-luminous without electrical control. The light emitting components are, for example, Light Emitting Diodes (LEDs), Organic Light Emitting Diodes (OLEDs), or other suitable self-luminous electronically-controlled light emitting components. The fluorescent members include fluorescent materials. The disclosure is not limited thereto. A beam emitted by the first light emitting member 126 is referred to as a sensing beam SB. A motion state of the patterns 124 may be sensed by the sensing beam SB. In the present embodiment, the first light emitting members 126 are, for example, integrated into the patterns 124 respectively. Therefore, each pattern 124 may also be regarded as a light emitting pattern.

The sensors 128 are configured to sense the motion state of the patterns 124, so as to obtain a motion-state sensing result about the flexible insertion tube 110. In the present embodiment, the sensors 128 are, for example, light sensors capable of converting an optical signal into an electrical signal, which may be, for example, a photodiode. The sensors 128 are disposed in the housing 122 and located beside the guiding hole GH. Moreover, according to measuring different motion states, the sensors 128 may be further divided into a plurality of depth sensors 1281 and a plurality of rotating angle sensors 1282. The depth sensors 1281 are disposed along an extension direction of the guiding hole GH and located beside the guiding hole GH. The rotating angle sensors 1282 are disposed around the guiding hole GH and located beside the guiding hole GH. How to sense the motion state of the patterns 124 will be described in detail in the following paragraphs.

The processor 129 is, for example, an electronic component capable of performing computation, processing or analysis functions on various electrical signals, such as a computer, a Micro Controller Unit (MCU), a Central Processing Unit (CPU), or other microprocessors, Digital Signal Processors (DSP), programmable controllers, Application Specific Integrated Circuits (ASIC), Programmable Logic Devices (PLD) or other similar devices. The processor 129 is disposed in the housing 122, electrically connected to the sensors 128, and configured to receive electrical signals from the sensors 128 to analyze the results.

The first and second circuit boards CB1, CB2 are disposed in the housing 122. The first circuit board CB1 is disposed in the vicinity of an opening of the guiding hole GH, and the guiding hole GH penetrates the first circuit board CB1. The second circuit board CB2 is disposed in the vicinity of a middle portion of the guiding hole GH, and the guiding hole GH penetrates the second circuit board CB2. The first and second circuit boards CB1, CB2 are arranged perpendicular to each other. The depth sensors 1281 are disposed on the first circuit board CB1 and electrically connected to the first circuit board CB1. The rotating angle sensors 1282 are disposed on the second circuit board CB2 and electrically connected to the second circuit board CB2. The processor 129 is electrically connected to the first and second circuit boards CB1, CB2, and receives electrical signals from the depth sensors 1281 and the rotating angle sensors 1282 through the first and second circuit boards CB1, CB2.

The timer T is an electronic component for measuring time, and is electrically connected to the processor 129.

The imaging device 130 is a photoelectric device for capturing an image inside the human body HB, and includes an imaging lens 132, a second light emitting member 134, and an image sensor 136. The imaging device 130 is disposed at an end E1 (for example, tail end) of the flexible insertion tube 110. The imaging lens 132 is, for example, a lens composed of one or more elements with refractive power, which is adapted to receive an image and optically coupled to the image sensor 136. The description of the second light emitting member 134 is similar to that of the first light emitting member 126. The description will be omitted herein. The second light emitting member is configured to emit an illumination beam IB for illuminating an object OB (for example, an organ) to be detected inside the human body HB.

The steering lever 140 is a mechanism member for controlling a motion in the flexible insertion tube 110. The steering lever 140 is disposed at the other end E2 (that is, different from the arrangement end E1 of the imaging device 130) of the flexible insertion tube 110 and coupled to the flexible insertion tube 110. By controlling an angle of a distal segment DS through the steering lever 140, the location of the imaging device 130 adjacent to the distal segment DS may be changed to further detect images of different organs.

In the following paragraphs, the operation mode of the endoscopy system 100 and how to specifically sense the motion-state sensing result of the patterns 124 in the motion sensing module 120 will be explained in detail.

First, the operation mode of the endoscopy system 100 will be described.

Referring to FIG. 1A, a patient may bite a biting portion BP extending below the housing 122 to prevent a user from damaging the flexible insertion tube 110 and fix the motion sensing module 120 above the mouth of the user. The flexible insertion tube 110 may be guided into the human body HB through the guiding hole GH. After the flexible insertion tube 110 enters the human body HB, the second light emitting member 134 emits an illumination beam IB to illuminate an object OB to be detected (for example, an organ) inside the human body HB. The object OB to be detected reflects at least a part of the illumination beam IB to the imaging lens 132, and the image sensor 136 senses an image. The image sensor 136 may transmit the image to a back-end display device (not shown) for medical personnel to observe a dynamic image inside the human body HB. In the process of entering the human body HB, medical personnel may directly control an angle of a bending segment BS of the flexible insertion tube 110 through the steering lever 140. Since the distal segment DS of the flexible insertion tube 110 is connected to the bending segment BS, the steering lever 140 may indirectly control the angle of the distal segment DS, and the imaging device 130 may observe different organs in the human body HB as the angle of the distal segment DS changes.

According to the above description, the medical personnel will extend the flexible insertion tube 110 into the human body through the guiding hole GH, and may control the angle of the distal segment by the steering lever 140 to observe different organs inside the human body. The above method results in a relative motion of the flexible insertion tube 110 with respect to the motion sensing module 120. The relative motion includes an axial motion of the flexible insertion tube 110 along the central axis CA and a rotating motion of the flexible insertion tube 110 with respect to the motion sensing module 120. That is, the motion sensing result of the patterns 124 includes an axial motion sensing result and a rotating motion sensing result. In the following paragraphs, FIG. 2A to FIG. 2C are used to explain in sections how the motion sensing module 120 senses an axial motion and a rotating motion.

Figure 2B:
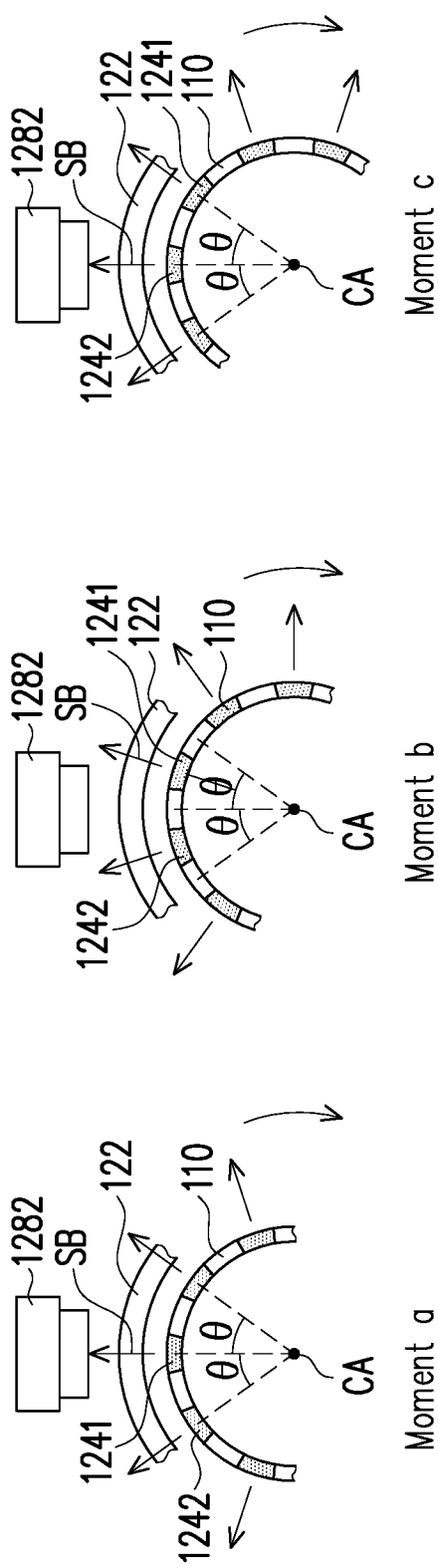
FIG. 2B is a schematic enlarged diagram of the flexible insertion tube of FIG. 1A to FIG. 1C during a rotating motion and a time-varying diagram of a light intensity electrical signal measured by a corresponding rotating angle sensor.
Figure 2B:
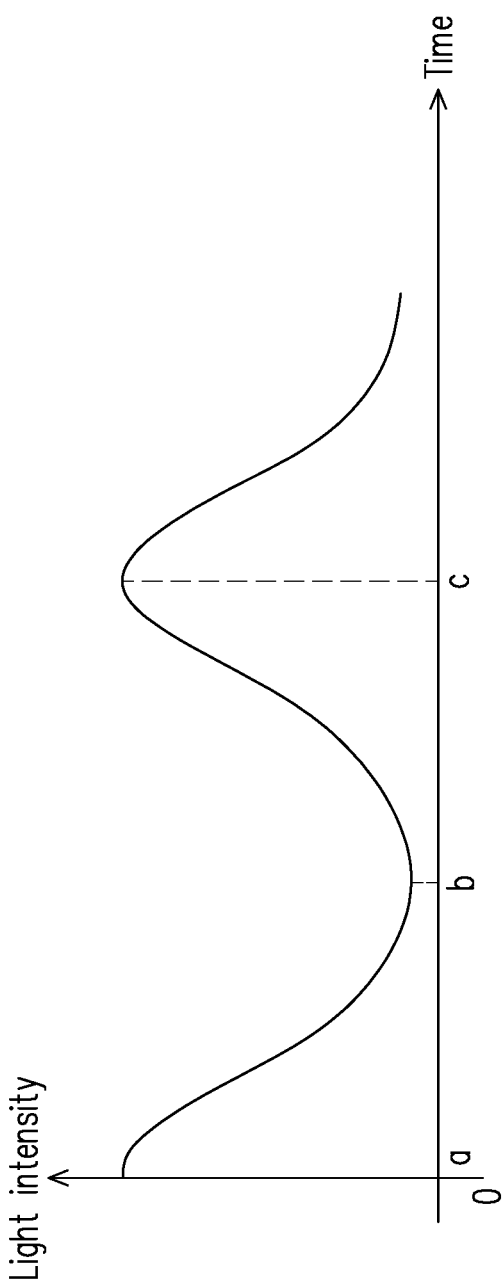

FIG. 2A is a schematic enlarged diagram of the flexible insertion tube of FIG. 1A to FIG. 1C during an axial motion and a time-varying diagram of a light intensity signal measured by a corresponding depth sensor. FIG. 2B is a schematic enlarged diagram of the flexible insertion tube of FIG. 1A to FIG. 1C during a rotating motion and a time-varying diagram of a light intensity signal measured by a corresponding rotating angle sensor. FIG. 2C is a schematic diagram of a configuration relationship between a plurality of depth sensors and a plurality of patterns and a signal sensed by a depth sensor.

Regarding the mode of sensing an axial motion, a view of a single depth sensor 1281 is taken first. Referring to FIG. 2A, it is assumed that the sensing beams SB emitted by the patterns 124 are integrated into an integrated sensing beam, and it is assumed that the location of the depth sensor 1281 initially corresponds to the center of a pattern 1241 (here labeled 1241, as a light emitting pattern). At this time, the depth sensor 1281 senses a maximum integrated sensing beam light intensity, shown at moment a in FIG. 2A. As the flexible insertion tube 110 travels toward the inside of the human body HB, and assuming that the location of the depth sensor 1281 corresponds to the centers of two patterns 1241, 1242, the depth sensor 1281 senses a minimum integrated sensing beam light intensity, shown at moment b in FIG. 2A. Then, as the flexible insertion tube 110 travels further toward the inside of the human body HB, and assuming that the location of the depth sensor 1281 corresponds to the center of a next pattern 1242, the depth sensor 1281 senses a maximum integrated sensing beam light intensity again, shown at moment c in FIG. 2A. Therefore, for a single depth sensor 1281, as long as the maximum integrated sensing beam light intensity is sensed twice, the size of a distance D by which the flexible insertion tube 110 moves along the axial orientation may be determined. However, other depth sensors 1281 may not be able to sense the maximum integrated sensing beam light intensity twice. Therefore, the back-end processor 129 will perform an operation according to all signal results measured by the depth sensor 1281 to obtain insertion depth information.

Regarding the mode of sensing a rotating motion, referring to FIG. 2B, which is similar to the description of FIG. 2A, it is assumed that the sensing beams SB emitted by the patterns 124 are integrated into an integrated sensing beam, and it is assumed that the location of the rotating angle sensor 1282 initially corresponds to the center of a pattern 1241 (here labeled 1241, as a light emitting pattern). At this time, the rotating angle sensor 1282 senses a maximum integrated sensing beam light intensity, shown at moment a in FIG. 2B. As the flexible insertion tube 110 rotates, for example, the motion sensing module 120 clockwise so that the location of the rotating angle sensor 1282 corresponds to the centers of two patterns 1241, 1242, the rotating angle sensor 1282 senses a minimum integrated sensing beam light intensity, shown at moment b in FIG. 2B. Then, as the flexible insertion tube 110 rotates, for example, the motion sensing module 120 clockwise again so that the location of the rotating angle sensor 1282 corresponds to the center of a pattern 1242, the rotating angle sensor 1282 senses a maximum integrated sensing beam light intensity again, shown at moment c in FIG. 2B. Therefore, for a single rotating angle sensor 1282, as long as the maximum integrated sensing beam light intensity is sensed twice, the size of an angle θ by which the flexible insertion tube 110 rotates clockwise may be determined. However, other rotating angle sensors 1282 may not be able to sense the maximum integrated sensing beam light intensity twice. Therefore, the back-end processor 129 will perform an operation according to all signal results measured by the rotating angle sensor 1282 to obtain insertion tube rotating angle information.

In addition to considering the above factors, the processor 129 will also consider phase factors of the signals measured by the sensors 128 to obtain more accurate insertion depth information and insertion tube rotating angle information. Referring to FIG. 1C, a spatial frequency of the sensors 128 and a spatial frequency of the patterns 122 are different from each other. That is, for the depth sensors 1281, a distance between the two depth sensors 1281 is different from a distance between the two patterns 124 disposed along the axial orientation of the central axis CA. For the rotating angle sensors 1282, an included angle between the two rotating angle sensors 1282 relative to the central axis CA is different from an included angle between the two patterns 124 relative to the central axis CA. Referring to FIG. 2C, a plurality of depth sensors 1281 (for example, but not limited to, 9) and a plurality of patterns 124 (for example, but not limited to, 10) are used as examples for description. It can be seen from this figure that the distance between the two depth sensors 1281 is different from the distance between the two patterns 124. Based on the above configuration, light intensity signal phases measured by each of depth sensors 12811-12819 are more or less different (here only the examples of signals S1-S5 detected by depth sensors 12811-12815 are shown here). Therefore, the processor 129 may further generate a depth coding function for the depth sensors 12811-12819 according to different signal phases, thereby obtaining more accurate insertion depth information. Similar to the method shown in FIG. 2C, the processor 129 may also further generate an angle coding function for the rotating angle sensors 1282 according to different signal phases, thereby obtaining more accurate insertion rotating angle information.

After calculating the insertion depth information and the insertion tube rotating angle information, the processor 129 may integrate the above information to obtain the location of a lesion, and note it in image information for reference by medical personnel. Moreover, the processor 129 may further output the above image and related information to a 3D model manufacturing machine (not shown) for the 3D model manufacturing machine to build an internal model of the human body HB, or as a basis for advanced image processing.

It is to be noted that the above calculation mode is only an example, and in other embodiments, the same parameters (i.e., axial orientation distribution, angle distribution and motion-state sensing result) may also be used to obtain insertion depth information and insertion tube rotating angle information by using different calculation modes. The disclosure is not limited thereto.

Based on the foregoing, in the endoscopy system 100 according to the present embodiment, a plurality of patterns 124 of a motion sensing module 120 is disposed at a surface S of a flexible insertion tube 110 according to an axial orientation distribution and an angle distribution, and a plurality of sensors 128 is disposed in a housing 122 and located beside a guiding hole GH. During the relative motion of the flexible insertion tube 110 with respect to the motion sensing module 120 via the guiding hole GH, the sensors 128 may sense a motion state of the patterns 124 so as to obtain a motion-state sensing result. The processor 129 then determines insertion depth information and insertion tube rotating angle information according to the motion-state sensing result, the axial orientation distribution and the angle distribution. Medical personnel may know the location of a lesion from the insertion depth information and the insertion tube rotating angle information. During the next diagnosis and treatment for the patient, the medical personnel may quickly find the lesion according to the previous measurement result, so the endoscopy system 100 may achieve accurate medical treatment.

Further, the processor 129 may further determine speed information and angular speed information of the flexible insertion tube 110 according to time information obtained by the timer T and the insertion depth information and the insertion tube rotating angle information, respectively.

In addition, in the present embodiment, the endoscopy system 100 may further optionally include first to third angle sensors AG1-AG3. In the following paragraphs, the arrangement locations and corresponding functions of the first to third angle sensors AG1-AG3 will be described in detail.

As shown in FIG. 1C, the first angle sensor AG1 is disposed in the housing 122 and electrically connected to the processor 129. The first angle sensor AG1 is configured to sense first angle information of the motion sensing module 120 and transmit the first angle information to the processor 129. Therefore, the processor 129 may obtain a horizontal angle, a vertical angle, a tilt angle, or a vibration state of the motion sensing module 120 according to the first angle information, and further calculate the locations of the flexible insertion tube 110 and the lesion. Moreover, the processor 129 may further obtain a change situation of the motion state during the diagnosis and treatment process according to the first angle information and the time information of the timer T.

As shown in FIG. 1A, the second angle sensor AG2 is disposed at an end E1 of the flexible insertion tube 110 and located beside the imaging device 130. The second angle sensor AG2 is electrically connected to the processor 129 and configured to sense second angle information of the end E1 of the flexible insertion tube 110. Since the second angle sensor AG2 is closer to the imaging device 130, the second angle information sensed by the second angle sensor may further improve the sensing accuracy of the motion sensing module 120.

As shown in FIG. 1A, the third angle sensor AG3 is disposed on the steering lever 140. The third angle sensor 140 is electrically connected to the processor 129 and configured to sense third angle information of the steering lever 140 to simply sense a rotating angle of the flexible insertion tube 110.

It must be noted here that the following embodiments follow the partial content of the foregoing embodiments, and the description of the same technical content is omitted. For the same component names, reference may be made to the partial content of the foregoing embodiments, and the following embodiments are not repeated.

Figure 3A:
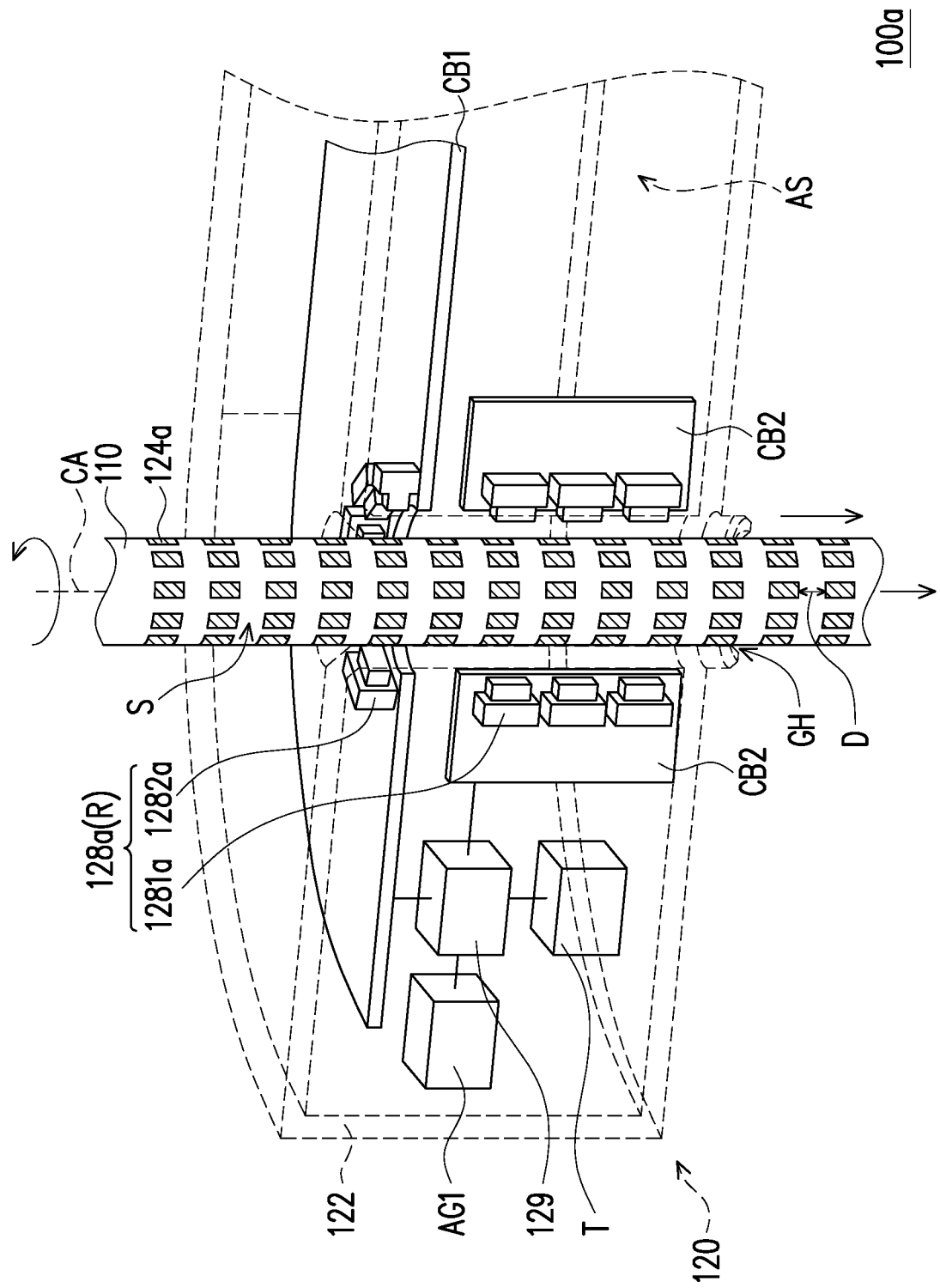
FIG. 3A is a schematic partial cross-sectional diagram of an endoscopy system according to another embodiment of the disclosure.
Figure 3B:
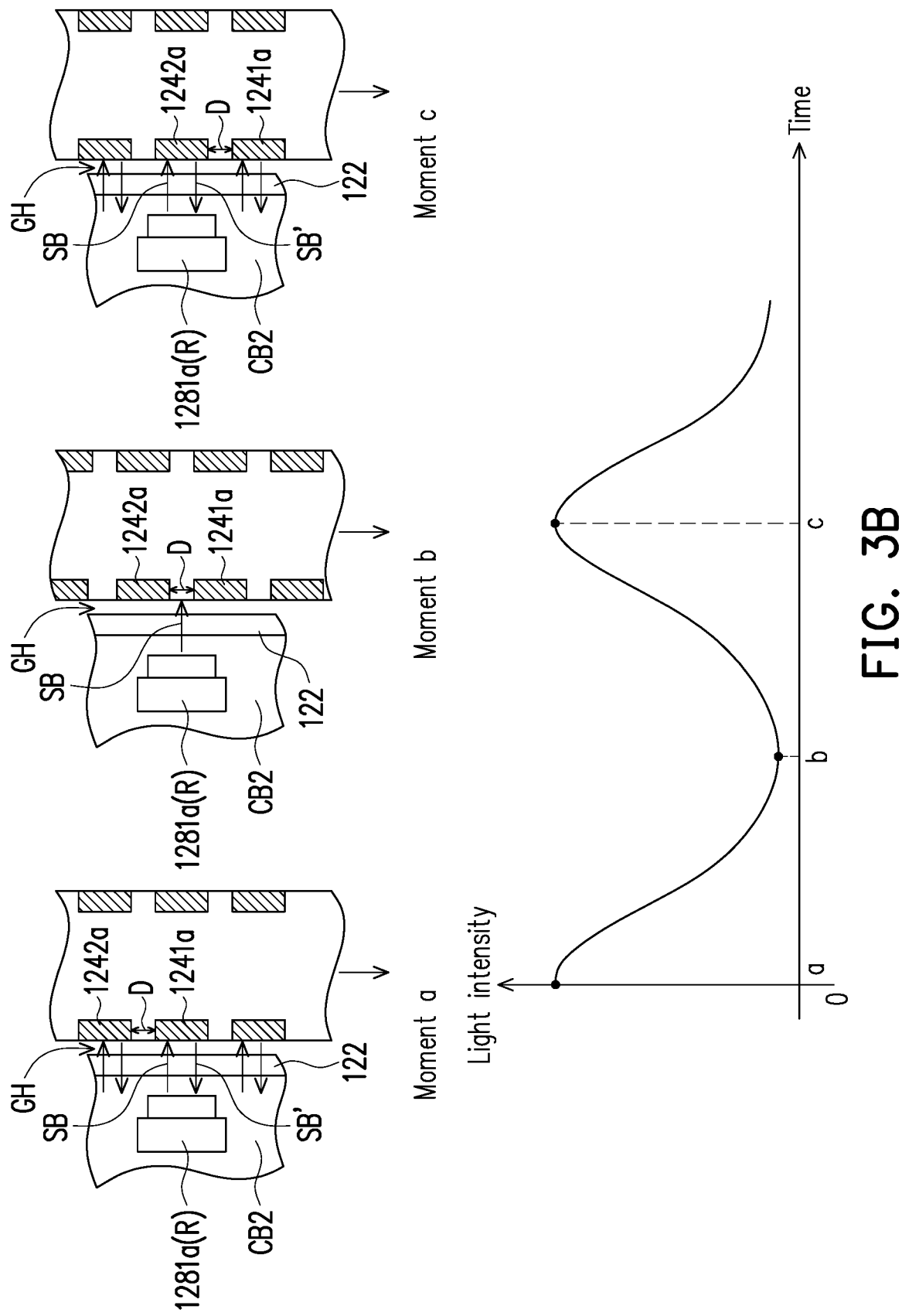
FIG. 3B is a schematic enlarged diagram of the flexible insertion tube of FIG. 3A during an axial motion and a time-varying diagram of an electrical signal measured by a corresponding depth sensor.
Figure 3C:
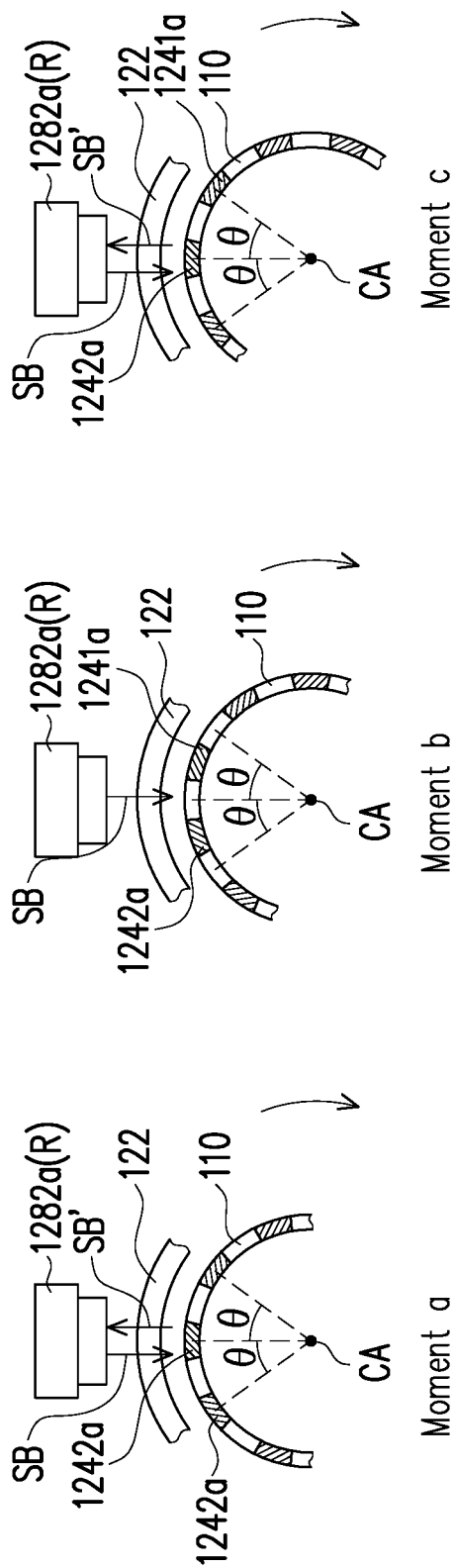
FIG. 3C is a schematic enlarged diagram of the flexible insertion tube of FIG. 3A during a rotating motion and a time-varying diagram of an electrical signal measured by a corresponding rotating angle sensor.
Figure 3C:
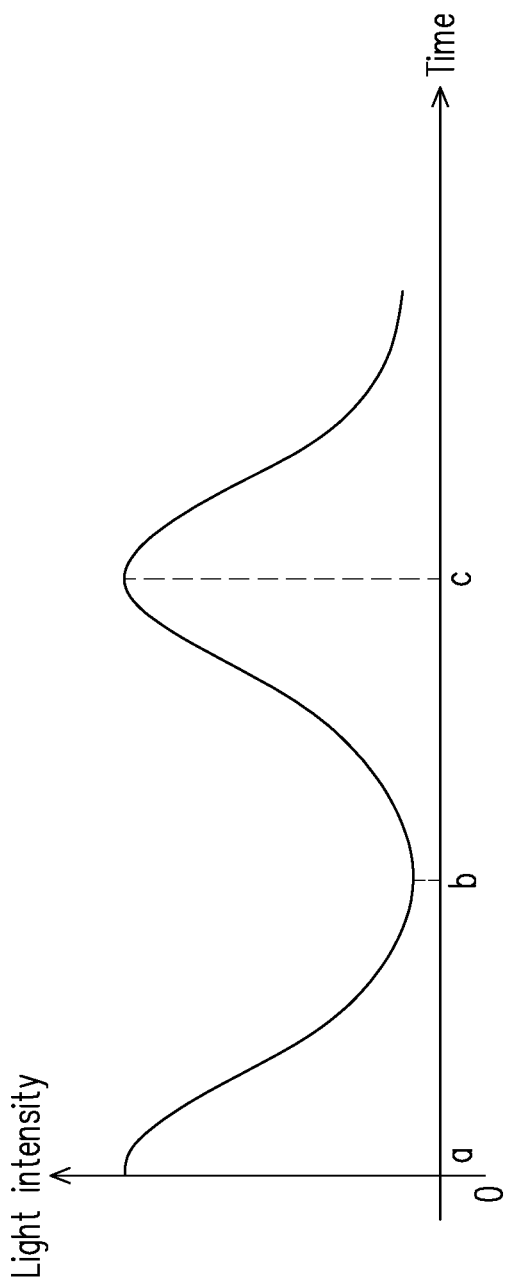

FIG. 3A is a schematic partial cross-sectional diagram of an endoscopy system according to another embodiment of the disclosure. FIG. 3B is a schematic enlarged diagram of the flexible insertion tube of FIG. 3A during an axial motion and a time-varying diagram of an electrical signal measured by a corresponding depth sensor. FIG. 3C is a schematic enlarged diagram of the flexible insertion tube of FIG. 3A during a rotating motion and a time-varying diagram of an electrical signal measured by a corresponding rotating angle sensor.

Referring to FIG. 3A to FIG. 3C, an endoscopy system 100*a* in FIG. 3A is substantially similar to the endoscopy system 100 in FIG. 1A to FIG. 1C. The main difference is that a motion sensing module 120a in the endoscopy system 100a is a reflective optical motion sensing module. In detail, the patterns are reflection patterns 124a having a reflection function, and the first light emitting elements (not shown in FIG. 3A) are integrated with the sensors 128 (light sensors) respectively. Therefore, each of the first light emitting elements and the corresponding sensor 128 constitute an optical transceiver sending module R.

Referring to FIG. 3B and FIG. 3C, the optical principle of the endoscopy system 100a of the present embodiment is slightly different from the optical principle of the endoscopy system 100. The difference is that during the relative motion of the flexible insertion tube 110 with respect to the motion sensing module 120 via the guiding hole GH, the first light emitting members 126 respectively emit a plurality of sensing beams SB (briefly shown as one) from where the light sensors 128 are located. Sensing beams SB' reflected by the reflection patterns 124a are transmitted to the depth sensors 1281 and the rotating angle sensors 1282 to obtain an axial motion sensing result and a rotating motion sensing result. The description of the measurement is similar to the related description of FIG. 2A to FIG. 2C and will be omitted herein.

Figure 4A:
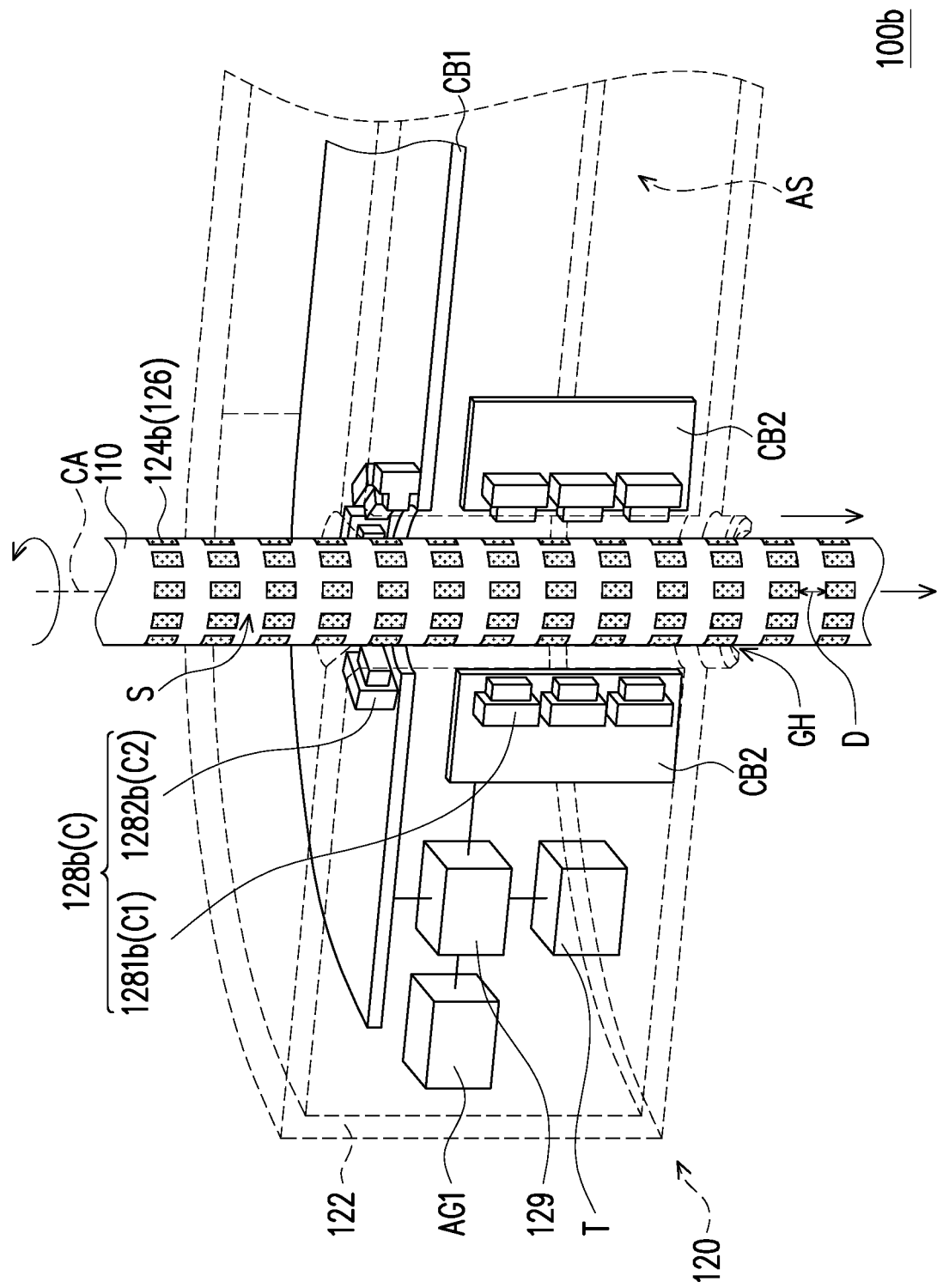
FIG. 4A is a schematic partial cross-sectional diagram of an endoscopy system according to yet another embodiment of the disclosure.
Figure 4C:
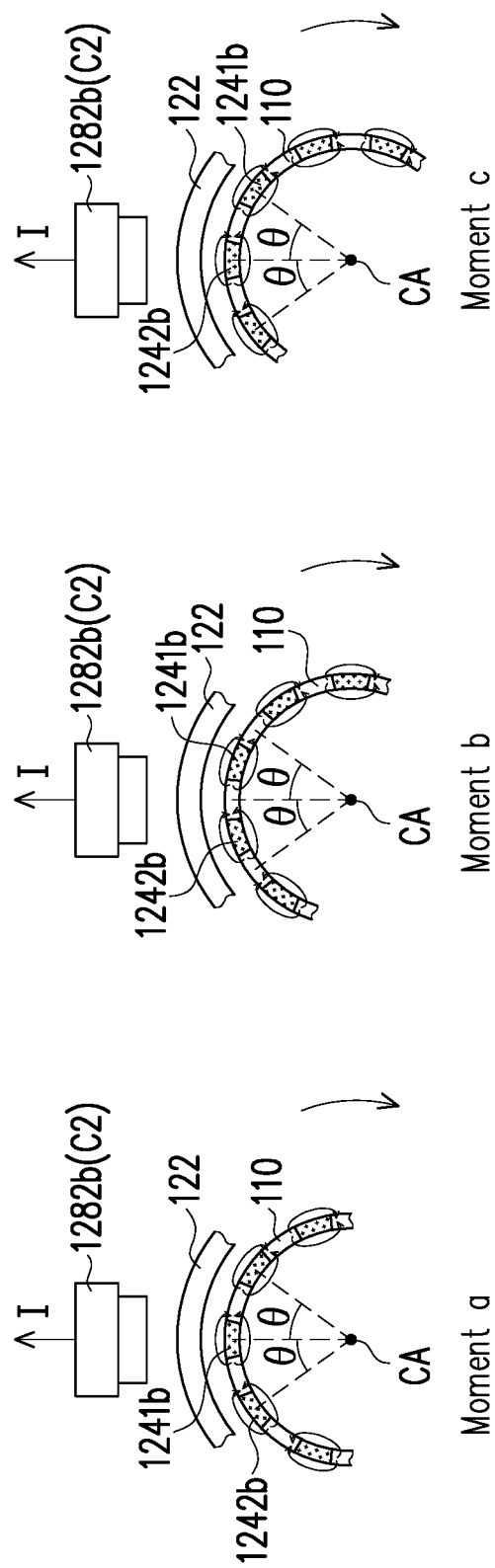
FIG. 4C is a schematic enlarged diagram of a rotating angle sensor corresponding to the flexible insertion tube of FIG. 4A during a rotating motion and a time-varying diagram of an electrical signal measured by a corresponding rotating angle sensor.
Figure 4C:
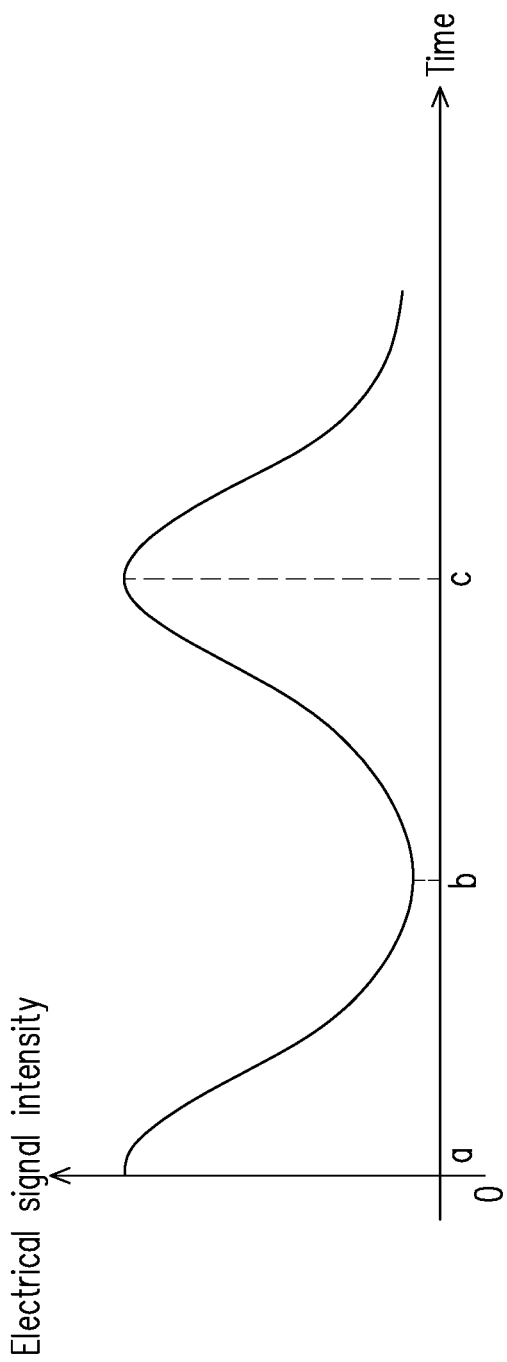

FIG. 4A is a schematic partial cross-sectional diagram of an endoscopy system according to yet another embodiment of the disclosure. FIG. 4B is a schematic enlarged diagram of the flexible insertion tube of FIG. 4A during an axial motion and a time-varying diagram of an electrical signal measured by a corresponding depth sensor. FIG. 4C is a schematic enlarged diagram of a rotating angle sensor corresponding to the flexible insertion tube of FIG. 4A during a rotating motion and a time-varying diagram of an electrical signal measured by a corresponding rotating angle sensor.

An endoscopy system 100b in FIG. 4A is substantially similar to the endoscopy system 100 in FIG. 1A to FIG. 1C. The main difference is that a motion sensing module 120b in the endoscopy system 100b is a magnetic field motion sensing module. In detail, the patterns are a plurality of magnetic patterns 124b, and the sensors 128b are a plurality of induction coils C. That is, the depth sensors 1281b are a plurality of depth induction coils C1, and the rotating angle sensors 1282b are a plurality of rotating angle induction coils C2. For example, the magnetic pattern 124b has, but not limited to, two magnetic lines.

Referring to FIG. 4B and FIG. 4C, the measurement principle of the endoscopy system 100b in the present embodiment is slightly different from the measurement principle of the endoscopy system 100. The difference is that during the relative motion of the flexible insertion tube 110 with respect to the motion sensing module 120 via the guiding hole GH, the depth induction coils 1281b and the rotating angle sensors 1282b induce at least one induced current I due to a magnetic field change of the magnetic patterns 124b caused by the relative motion, and an axial motion sensing result and a rotating motion sensing result are obtained accordingly. In other words, the signal source mode of the motion sensing module 120b is an electrical signal converted by a magnetic field change, and the signal source mode of the motion sensing module 120b is an electrical signal converted by a sensing beam SB. The measurement mode of the motion sensing module 120b is substantially similar to the description of FIG. 2A and FIG. 2B. The description thereof is omitted herein.

In other embodiments not shown, the sensors 128b in the motion sensing module 120b in FIG. 4A may also be replaced with Hall sensors. That is, the depth sensors 1281b are a plurality of depth Hall sensors, and the rotating angle sensors 1282b are a plurality of rotating angle Hall sensors. Therefore, the depth sensors 1281b and the rotating angle sensors 1282b may sense a magnetic field change of the magnetic patterns 124b to induce at least one induced voltage, and an axial motion sensing result and a rotating motion sensing result are obtained accordingly.

Based on the foregoing, in the endoscopy system according to the embodiments of the disclosure, a plurality of patterns of a motion sensing module is disposed at a surface of a flexible insertion tube according to an axial orientation distribution and an angle distribution, and a plurality of sensors is disposed in a housing and located beside a guiding hole. Therefore, a distance or angle relationship specified by the patterns is used as a quantitative basis for the description of a location or a motion state. During the relative motion of the flexible insertion tube with respect to the motion sensing module via the guiding hole, the sensors may sense a motion state of the patterns so as to obtain a motion-state sensing result. The sensors may sense the motion state of the patterns by optical changes or magnetic field changes of the patterns. Moreover, the sensors are further divided into a plurality of depth sensors and a plurality of rotating angle sensors according to different sensing functions. The depth sensors are disposed in an extension direction of the guiding hole. The rotating angle sensors are disposed around the guiding hole. When the flexible insertion tube undergoes relative motion with respect to the motion sensing module, the depth sensors may be configured to sense an axial motion state of the patterns to determine insertion depth information of the flexible insertion tube into a human body. In addition, the rotating angle sensors may be configured to sense a rotating motion state of the patterns to determine insertion tube rotating angle information of the flexible insertion tube into the human body. During the next diagnosis and treatment for a patient, medical personnel may quickly find the lesion according to the previous measurement result, so the medical personnel may achieve accurate medical treatment by means of the endoscopy system of the disclosure.

Although the disclosure has been disclosed as above by way of embodiments, it is not intended to limit the disclosure. Any person with ordinary knowledge in the technical field can make some changes and decorations without departing from the spirit and scope of the disclosure, so the protection scope of the disclosure shall be determined by the scope of the attached patent application.

What is claimed is:

1. An endoscopy system obtaining insertion depth information and insertion tube rotating angle information, comprising:
  a flexible insertion tube, comprising a central axis;
  a motion sensing module, comprising:
    a housing, comprising a guiding hole;
    a plurality of patterns, disposed at a surface of the flexible insertion tube according to an axial orientation distribution and an angle distribution based on the central axis;
    a plurality of sensors, arranged in the housing and located beside the guiding hole, the sensors comprise a plurality of depth sensors and a plurality of rotating angle sensors, the depth sensors are arranged in an extension direction of the guiding hole, distances between two adjacent ones of the depth sensors are the same with each other, and the rotating angle sensors are arranged around the guiding hole; and
  a processor, disposed in the housing and electrically connected to the sensors, wherein during relative motion of the flexible insertion tube with respect to the motion sensing module via the guiding hole,
the sensors are configured to sense a motion state of the patterns so as to obtain a motion-state sensing result via a light intensity electrical signal, and the processor determines the insertion depth information and the insertion tube rotating angle information according to the motion-state sensing result, the axial orientation distribution and the angle distribution, and
a ratio of a spatial frequency of the depth sensors in the extension direction of the guiding hole to a spatial frequency of the patterns in the extension direction of the guiding hole is non-integral;
an imaging device, disposed at one end of the flexible insertion tube.

2. The endoscopy system according to claim 1, wherein the motion sensing module further comprises a plurality of first light emitting members, the sensors are a plurality of light sensors, and each of the first light emitting members is configured to emit a sensing beam.

3. The endoscopy system according to claim 2, wherein the first light emitting members are integrated into the patterns respectively so that the patterns are a plurality of light emitting patterns,
wherein during the relative motion of the flexible insertion tube with respect to the motion sensing module via the guiding hole,
the light emitting patterns emit the sensing beams from the flexible insertion tube to be transmitted to the depth sensors and the rotating angle sensors to obtain an axial motion sensing result and a rotating motion sensing result.

4. The endoscopy system according to claim 2, wherein the first light emitting members are integrated into the light sensors respectively, and the patterns are a plurality of reflection patterns,
wherein during the relative motion of the flexible insertion tube with respect to the motion sensing module via the guiding hole,
the first light emitting members emit the sensing beams to the reflection patterns from where the light sensors are located, the reflection patterns reflect the sensing beams, and the reflected sensing beams are transmitted to the depth sensors and the rotating angle sensors to obtain an axial motion sensing result and a rotating motion sensing result.

5. The endoscopy system according to claim 1, wherein the patterns are a plurality of magnetic patterns, the sensors are a plurality of induction coils, the depth sensors are a plurality of depth induction coils, and the rotating angle sensors are a plurality of rotating angle induction coils,
wherein during the relative motion of the flexible insertion tube with respect to the motion sensing module via the guiding hole,
the depth induction coils and the rotating angle induction coils sense a magnetic field change of the magnetic patterns to induce at least one induced current, and the depth induction coils and the rotating angle induction coils obtain an axial motion sensing result and a rotating motion sensing result according to the at least one induced current.

6. The endoscopy system according to claim 1, wherein the patterns are a plurality of magnetic patterns, the sensors are a plurality of Hall sensors, the depth sensors are a plurality of depth Hall sensors, and the rotating angle sensors are a plurality of rotating angle Hall sensors,
wherein during the relative motion of the flexible insertion tube with respect to the motion sensing module via the guiding hole,
the depth Hall sensors and the rotating angle Hall sensors sense a magnetic field change of the magnetic patterns to induce at least one induced voltage, and the depth Hall sensors and the rotating angle Hall sensors obtain an axial motion sensing result and a rotating motion sensing result according to the at least one induced voltage.

7. The endoscopy system according to claim 1, wherein the motion sensing module further comprises a first angle sensor, disposed in the housing and electrically connected to the processor,
wherein the first angle sensor is configured to sense first angle information of the motion sensing module and transmit the first angle information to the processor.

8. The endoscopy system according to claim 1,
wherein the motion sensing module further comprises a first circuit board and a second circuit board disposed in the housing, the first circuit board is electrically connected to the depth sensors, and the second circuit board is electrically connected to the rotating angle sensors.

9. The endoscopy system according to claim 1, wherein the motion sensing module further comprises a timer, and the timer is electrically connected to the processor and is configured to transmit time information to the processor,
wherein the processor determines speed information of the flexible insertion tube according to the time information and the insertion depth information, and
the processor determines angular speed information of the flexible insertion tube according to the time information and the insertion tube rotating angle information.

10. The endoscopy system according to claim 1, wherein the axial orientation distribution is an equal pitch distribution.

11. The endoscopy system according to claim 1, wherein the angle distribution is an equal angle distribution.

12. The endoscopy system according to claim 1, further comprising a second angle sensor, disposed at the end of the flexible insertion tube and located beside the imaging device, wherein the second angle sensor is electrically connected to the processor and is configured to sense second angle information of the end of the flexible insertion tube.

13. The endoscopy system according to claim 1, further comprising:
a steering lever, disposed at another end of the flexible insertion tube and coupled to the flexible insertion tube, wherein the steering lever is configured to control an angle of a distal segment in the flexible insertion tube.

14. The endoscopy system according to claim 13, further comprising a third angle sensor, disposed on the steering lever, wherein the third angle sensor is electrically connected to the processor and is configured to sense third angle information of the steering lever.

15. The endoscopy system according to claim 1, wherein the imaging device further comprises an imaging lens, a second light emitting member and an image sensor, wherein the imaging lens is optically coupled to the image sensor, the second light emitting member is configured to emit an illumination beam to illuminate an object to be detected, the object to be detected reflects at least a part of the illumination beam to the imaging lens, and the image sensor senses an image of the object to be detected.

16. The endoscopy system according to claim 8, wherein the second circuit board is disposed in a vicinity of a middle portion of the guiding hole and paralleled with the extension direction of the guiding hole.

17. The endoscopy system according to claim 1, wherein distances between the depth sensors and the central axis of the flexible insertion tube are the same with each other.

\* \* \* \* \*